(12) United States Patent
O'Gorman et al.

(10) Patent No.: US 6,970,584 B2
(45) Date of Patent: Nov. 29, 2005

(54) ENCLOSURE AND BIOMETRIC DATA COLLECTION FOR FINGERPRINT SENSOR DEVICE

(75) Inventors: Lawrence O'Gorman, Madison, NJ (US); Wayne H. Miller, Los Altos, CA (US)

(73) Assignee: UPEK, Inc., Emeryville, CA (US)

( * ) Notice: Subject to any disclaimer, the term of this patent is extended or adjusted under 35 U.S.C. 154(b) by 0 days.

(21) Appl. No.: 09/681,655

(22) Filed: May 16, 2001

(65) Prior Publication Data

US 2002/0172402 A1 Nov. 21, 2002

Related U.S. Application Data

(63) Continuation of application No. 09/169,894, filed on Oct. 12, 1998, now abandoned.

(51) Int. Cl.[7] .............................................. G06K 9/00
(52) U.S. Cl. ...................... 382/126; 340/340; 340/5.83
(58) Field of Search ........................ 382/115, 124, 126; 235/380, 492; 704/246, 273; 902/3, 4, 25; 340/5.82, 5.83; 283/68; 356/71

(56) References Cited

U.S. PATENT DOCUMENTS

| | | | |
|---|---|---|---|
| 3,804,524 A | 4/1974 | Jocoy et al. ................. 356/138 |
| 4,701,959 A | 10/1987 | Asai et al. ....................... 382/4 |
| 4,843,377 A | 6/1989 | Fuller et al. ................. 340/573 |
| 4,893,078 A | 1/1990 | Auchterlonie ................ 324/208 |
| 4,933,976 A | 6/1990 | Fishbine et al. ................ 382/4 |
| 5,003,260 A | 3/1991 | Auchterlonie .......... 324/207.16 |
| 5,177,802 A | 1/1993 | Fujimoto et al. ............... 382/4 |
| 5,473,144 A | 12/1995 | Mathurin, Jr. ............... 235/380 |

(Continued)

FOREIGN PATENT DOCUMENTS

EP 0 813 164 A1 12/1997 ............ G06K 9/00

(Continued)

*Primary Examiner*—Samir Ahmed
(74) *Attorney, Agent, or Firm*—DLA Piper Rudnick Gray Cary US LLP; Andrew V. Smith

(57) ABSTRACT

The enclosure assembly comprises a stationary member including at least two substantially parallel sidewalls, the sidewalls, the sidewalls partially defining a cavity in which the fingerprint sensor is disposed. An access piece, configured to move relative to the stationary member, has a surface area larger than the surface area of the fingerprint sensor and further includes a conductive portion electrically coupled to ground. A movement apparatus is preferably mechanically coupled to the stationary member and the moveable access piece. The movement apparatus is configured to maintain the moveable access piece in a position covering the fingerprint sensor and yet to allow motion of the moveable access piece relative to the stationary member so as to expose the fingerprint sensor. According to another embodiment, a method for enrolling a composite image of an object using a fingerprint sensor is provided. According to an embodiment, the method comprises the steps of receiving a finger disposed over a fingerprint sensor in a first stationary position; capturing a first image of a first portion of the finger with the fingerprint sensor; causing the finger to be repositioned over the fingerprint sensor in a second stationary position; capturing a second image of a second portion of the finger with the fingerprint sensor; and constructing a representative image of the finger from the first and second images.

20 Claims, 7 Drawing Sheets

U.S. PATENT DOCUMENTS

| | | | |
|---|---|---|---|
| 5,838,306 A | 11/1998 | O'Connor et al. | 345/163 |
| 5,920,640 A | 7/1999 | Salatino et al. | 382/124 |
| 5,942,761 A | 8/1999 | Tuli | 250/556 |
| 5,978,495 A * | 11/1999 | Thomopoulos et al. | 382/124 |
| 6,164,540 A | 12/2000 | Bridgelall et al. | 235/462.01 |

FOREIGN PATENT DOCUMENTS

| | | | |
|---|---|---|---|
| GB | 1 267 996 A | | 3/1972 |
| JP | 64-65676 | * | 3/1989 |
| JP | 4-88586 | * | 3/1992 |

\* cited by examiner

ENCLOSURE AND BIOMETRIC DATA COLLECTION FOR FINGERPRINT SENSOR DEVICE

CROSS REFERENCE TO RELATED APPLICATIONS

This application is a continuation of U.S. patent application Ser. No. 09/169,894, filed Oct. 12, 1998, now abandoned to which priority is claimed under U.S.C. Section 120. Furthermore, this application is related to U.S. Pat. No. 6,049,620, filed May 13, 1997, entitled "Capacitive Fingerprint Sensor Device With Adjustable Gain," by Alexander G. Dickinson et al., and to U.S. patent application Ser. No. 08/971,455, filed Nov. 17, 1997, entitled "Automatic Adjustment Processing For Sensor Devices," by inventors Lawrence O'Gorman et al. Each of the three above referenced patent and patent applications are incorporated herein by reference in their entirely.

BACKGROUND OF INVENTION

1. Field of the Invention

The invention relates to enclosures and data collection for sensor devices, and more particularly to a protective enclosure, which also aligns an object placed on a biometric sensor.

2. Background Information

Biometric-oriented personal identification techniques are becoming increasingly important in protecting personal property, such as laptop computers and cellular phones, preventing credit card and calling card fraud, limiting access to security areas, computers and information, and ensuring security for electronic commerce.

Biometric identification techniques use physical traits, measurements and characteristics specific to an individual. These characteristics include, but are not limited to, voice prints, hand prints, fingerprints, retina patterns, and signatures. Typically, biometric identification and verification techniques compare an individual's stored biometric data (the enrolled data) against newly obtained biometric data when the individual desires use of a protected item, access to a protected area or access to protected information. Because biometric data is reasonably stable and not susceptible to being forgotten, biometric data has the advantage of being persistently available for user identification and verification.

A fingerprint biometric is one of the most widely deployed biometric identification techniques. Existing technology allows the relevant features of a fingerprint to be represented in a few hundred bytes of data. Furthermore, the computer hardware required for recording and comparing fingerprint data can be centralized and accessed through a telecommunications network, centralized databases, and processing hardware, with the result that costs may be amortized across many more transactions than would be the case for distributed processing.

There are, however, disadvantages to biometric identification and verification. For instance, biometric sensors, which are highly sensitive, are exposed to a number of environmental hazards, such as impact and electrostatic discharge.

There are also problems associated with acquiring an accurate image of the fingerprint image. In a typical enrollment procedure, the user centers the core of the fingerprint on the sensor, because the core portion of the finger provides desirable identification characteristics. Due to relatively small size of most fingerprint sensors, often as small as 0.6 inches square (150 mm by 150 mm), little, if any, of the fingerprint beyond this region is sensed by the sensor. During an access procedure, users instinctively place their fingertip on the sensor. When a fingerprint is positioned on the sensor that does not overlap the enrolled image, access will be denied due to finger placement error.

SUMMARY OF INVENTION

An enclosure assembly for a fingerprint sensor is provided. The enclosure assembly comprises a stationary member including at least two substantially parallel sidewalls, the sidewalls partially defining a cavity in which the fingerprint sensor is disposed. An access piece, configured to move relative to the stationary member, has a surface area larger than the surface area of the fingerprint sensor and further includes a conductive portion electrically coupled to ground. A movement apparatus is preferably mechanically coupled to the stationary member and the moveable access piece. The movement apparatus is configured to maintain the moveable access piece in a position covering the fingerprint sensor and yet to allow motion of the moveable access piece relative to the stationary member so as to expose the fingerprint sensor.

In another embodiment, the enclosure assembly further comprises an image quality indictor communicatively coupled to the fingerprint sensor and configured to signal whether biometric information collected by the fingerprint sensor is acceptable. In yet another embodiment, the enclosure assembly further comprises a switch that electrically couples a power supply to the fingerprint sensor after the moveable access piece exposes a portion of the cavity.

According to another embodiment, a method for enrolling a composite image of an object using a fingerprint sensor is provided. According to an embodiment, the method comprises the steps of receiving a finger disposed over a fingerprint sensor in a first stationary position; capturing a first image of a first portion of the finger with the fingerprint sensor; causing the finger to be repositioned over the fingerprint sensor in a second stationary position; capturing a second image of a second portion of the finger with the fingerprint sensor; and constructing a representative image of the finger from the first and second images.

BRIEF DESCRIPTION OF DRAWINGS

For a better understanding of the invention, reference is made to the accompanying drawings, in which.

DETAILED DESCRIPTION

Provided is an apparatus and method for enclosing and operating a biometric sensor. An enclosure protects the sensor from harmful impacts, from electrostatic discharges (ESDs), and from other environmental hazards. In a preferred embodiment, the enclosure protects a biometric sensor used for sensing fingerprints, and the enclosure is configured to cause a fingerprint core to properly align with the sensor during an access procedure. In another embodiment, an apparatus is provided for indicating to the user when a fingerprint image of adequate quality is captured. The enclosure is also used during enrollment, and a method is provided for enrolling and reconstructing a fingerprint image that increases the likelihood of image overlap during an access procedure.

Figure 1A:
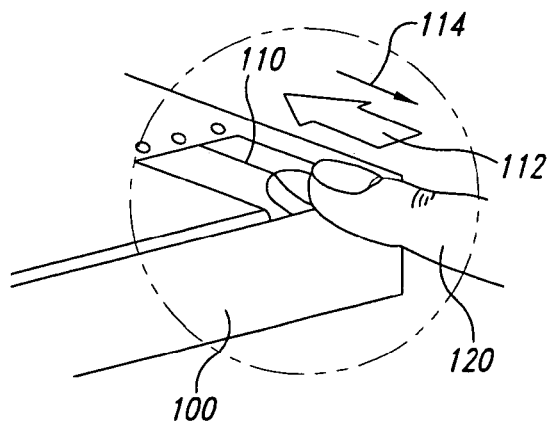
FIG. 1A shows one view of a first exemplary enclosure.
Figure 1B:
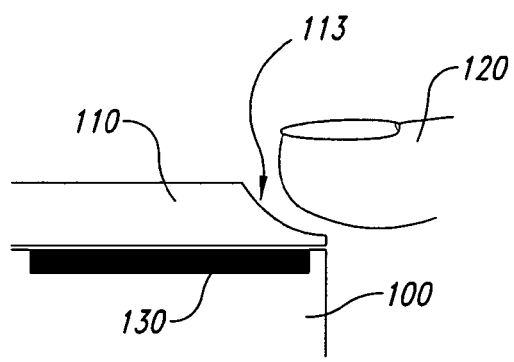
FIG. 1B shows a cross-sectional view of the enclosure of FIG. 1A.

The preferred embodiment of the enclosure is shown in FIG. 1A. The enclosure 100 comprises and access piece 110 which is shown in the closed position. The access piece 110 is a sliding door, which is movable in the direction of arrows 112 and 114. A cross-section of the enclosure 100 with the access piece 110 in a closed position is shown in FIG. 1B. A sensor 130 is mounted in the enclosure 100 such that the closed access piece 110 covers the sensor 130, thereby protecting it from impacts. An exemplary embodiment of a fingerprint sensor device 130 that can be used in conjunction with the enclosure 100 is explained in U.S. Pat. No. 6,049,620, entitled "Capacitive Fingerprint Sensor Device With Adjustable Gain", which was incorporated herein by reference in its entirety above.

Figure 1C:
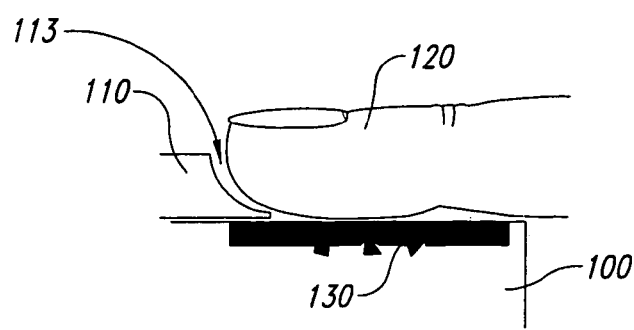
FIG. 1C shows another cross-sectional view of the enclosure of FIG. 1A.

Operation of the enclosure 100 is described with reference to FIGS. 1A–1C. A user accesses the sensor 130 by placing a finger 120 on the access piece 110 and moving it in the direction of arrow 112. In this position, the sensor 130 is fully revealed, as shown in FIG. 1C, and the finger 120 has access to the sensor 130. The finger 120 will then be disposed on the sensor 130 in a proper position and the sensing operation may proceed. A spring (not shown) attaches the access piece 110 to the enclosure 100 such that the access piece 110 closes (i.e., it is returned to the closed position) when the finger is removed.

To overcome the hazards of ESD to the sensor 130, especially during the access procedure, the access piece 110 comprises a conductive material that is electrically grounded. When a finger touches the access piece 110 to access the sensor 130, the finger is grounded through the conductive portion of the access piece 110. Because the finger 120 must continue to apply pressure to the access piece 110 to overcome the force of the spring, the finger 120 remains grounded throughout the sensing operation. Once the finger is removed from the access piece 110, it automatically closes, thereby covering the sensor 130.

Figure 1D:
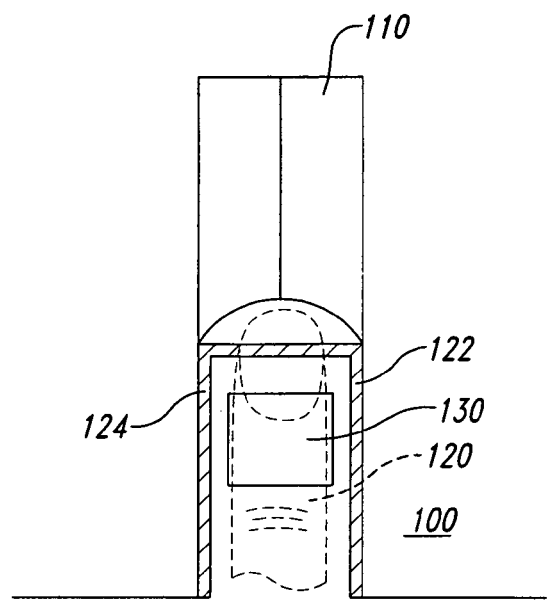
FIG. 1D shows a top view of the enclosure of FIG. 1A.
Figure 1E:
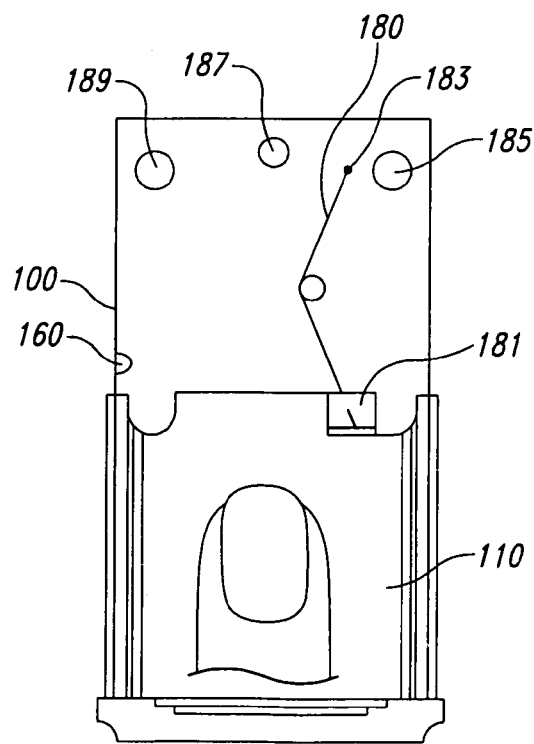
FIG. 1E shows view of a second exemplary enclosure.

One exemplary spring configuration is shown in FIG. 1E. The spring 180 is a coil spring with elongated ends, each end having a hook. At one end, the spring 180 is hooked to a coupling protrusion 181 on the access piece 110. The other end is hooked to the enclosure 100 at an aperture 183. When the spring 180 is relaxed (that is, not under tension), the access piece 110 is closed.

As shown in FIG. 1E, the enclosure can further comprise a mechanism for mechanically fastening the enclosure 100 to some other device, such as a laptop computer. In the illustrated embodiment, a fastening apparatus includes a locating pin 187 and fastening holes 185 and 189. The locating pin 187 fits in a corresponding hole in the device of interest to locate the enclosure 100 in the desired position. Fastening holes 185 and 189 are configured to accept a corresponding fastening apparatus, such as a screw.

According to one embodiment, a switch 160 attached to the enclosure 100 is also provided. The switch 160 operates to switch power to the sensor on or off. The switch 160 is positioned relative to the access piece 110 so that the access piece 110 engages the switch when the user slides the access piece 110, to access the sensor (not shown in FIG. 1E). When the user releases the access piece 110, the spring 180 causes the access piece 110 to return to the closed position. After or during movement of the access piece 110 to the closed position, the access piece 110 caused the switch 160 to disengage power from the sensor.

It is another advantage of an embodiment of the enclosure 100 that the access piece 110 is configured to stop in a position that aligns the finger 120 with the sensor 130. Referring to the cross-section of the access piece shown in FIG. 1B, the access piece 110 is shaped to form a fingertip contour 113. As a user approaches the enclosure 100 to access the sensor 130, the user intuitively touches the access piece 110 in this contoured area 113 with the finger tip, because the fingertip naturally fits into the area 113. As shown in FIG. 1C, when the access piece 110 is moved to an open position with the fingertip placed in the contoured area 113, the top of the finger 120 extends beyond the sensor 130 and the fingerprint core is aligned with the sensor 130.

Lateral alignment of the finger 120 on the sensor 130 is shown with reference to FIG. 1D. The enclosure 100 comprises guides 122 and 124 spaced apart by a predetermined width, preferably the width of the finger 120. In the enclosure 100, the guides 122 and 124 are molded plastic walls. To accommodate fingers of various sizes, the walls may also be slanted inwardly from top to bottom; that is, toward the sensor.

When the finger 120 is placed on the sensor 130, the guides laterally align the finger 120 on the sensor 130. The alignment provided by the access piece 110 in the open position and by the guides 122 and 124 enhances accuracy and reliability in acquiring the fingerprint image by minimizing finger placement error (e.g., orientation).

Figure 2:
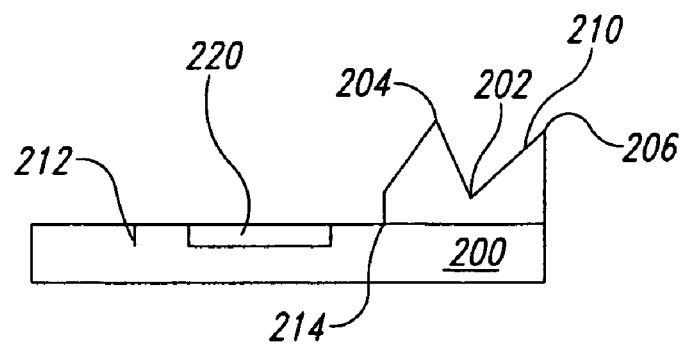
FIG. 2 shows a side view of a third exemplary enclosure.

Of course, the access piece may be configured in various ways to protect sensors designed for various uses. For instance, with reference to FIG. 2, a side view of an enclosure 200 comprising a hinged 202, 204 and 206 access piece 210 is shown. The access piece 210 is positionable at a closed position 212 and an open position 214. In the closed position 212, a sensor 220 is covered, protecting it from impacts. To move the access piece 210, the user pushes the access piece 110 with his finger to the open position 214. The same previously described alignment and grounding features can be provided.

Figure 3:
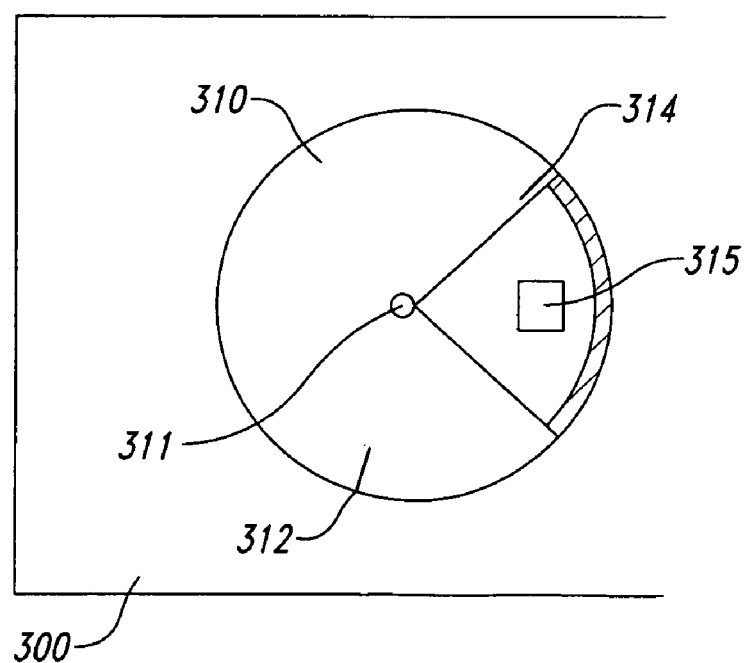
FIG. 3 shows a top view of a fourth exemplary enclosure.

The top view of another embodiment is shown in FIG. 3. The enclosure 300 comprises a rotatable access piece 310 that is positionable at a closed position 312 and at an open position 314. The user operates the access piece 310 by rotating it with his finger, about a pivot 311, to the open position 314 to expose sensor 315. As in the preferred embodiment, the access piece 310 is electrically conductive to ground, and is configured to return to the closed position when the finger is removed from the access piece 310.

Figure 4A:
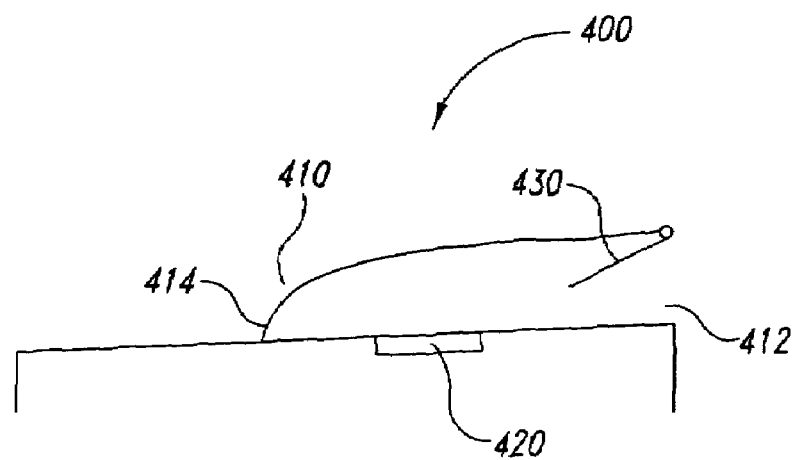
FIGS. 4A and 4B show side view and perspective views, respectively, of a fifth exemplary enclosure.
Figure 4B:
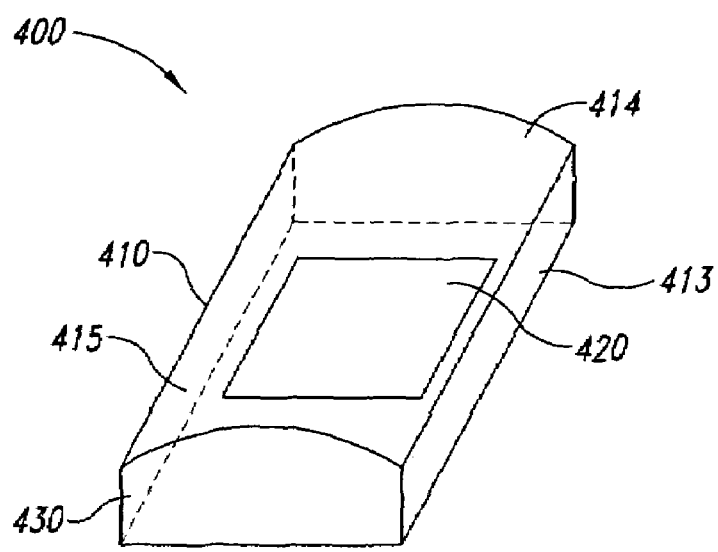

Still another configuration is shown in FIGS. 4A and 4B. An enclosure 400 comprises a housing 410 with an access end 412 and a closed end 414. The housing 410 protects a sensor 420 from impacts when the sensor 420 is not in use. An access piece 430 covers the access end 412. The access piece 430 is swingable between a closed position (not shown) and an open position. The sensor 420 is accessed by pushing on the access piece 430 with his finger. The access piece 430 is grounded, again protecting the sensor 420 from ESD. Preferably, the housing 410 is shaped such that a finger placed within the housing is laterally aligned with the sensor 420. In this embodiment, the closed end 414 of the housing 410 acts as a stop, causing the finger to be aligned with the sensor 420 such that the core of the fingerprint is on the sensor 420.

A perspective of this configuration is shown in FIG. 4B. Walls 413 and 415 laterally constrain the finger (not shown) such that the finger is laterally aligned on the sensor 420. The closed end 414 acts as a constraint causing the fingerprint core to locate on the sensor 414. The access piece 430 is grounded to protect the sensor 420 from the electrostatic discharge.

Figure 8A:
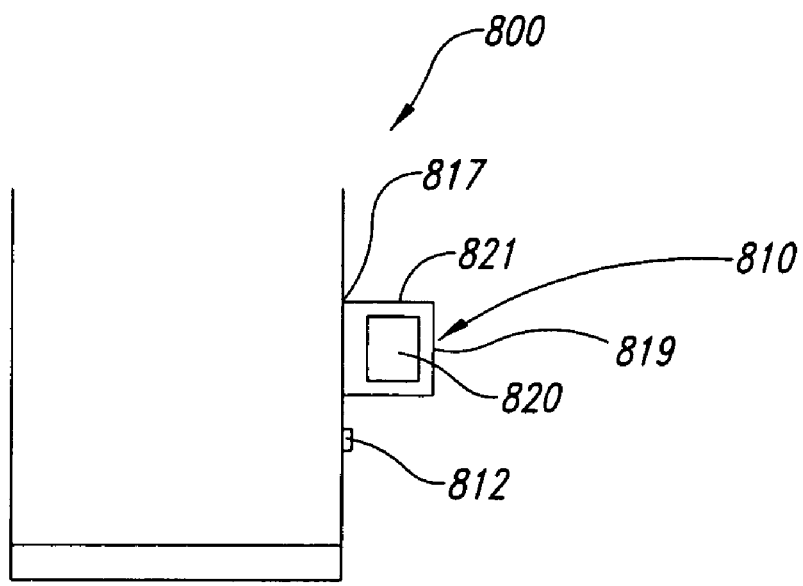
FIGS. 8A and 8B show another exemplary embodiment of the enclosure.
Figure 8B:
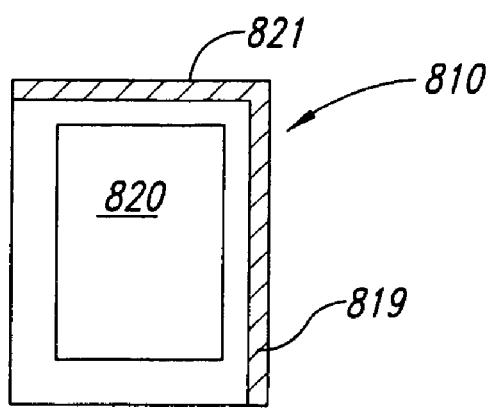

In still another configuration, the sensor is mounted in a slidable unit. As shown in FIG. 8A and FIG. 8B, the enclosure 800 comprises a sliding unit 810. In the closed position, the sliding unit 810 resides within the enclosure 800 and the sensor 820 is protected. An access piece 812, which is a button in this configuration, is operable to cause the sliding unit 810 to slide out of the enclosure 800. The mechanics for sliding the sliding unit 810 into and out of the enclosure 800 can be a spring or motor. As in the prior configurations, the button 812 is electrically conductive to a ground. The user is grounded when the button 812 is pressed to release the sliding unit 810. An enclosure edge 817 constrains the finger in one direction and sliding unit edges 819 and 821 constrain the finger in a second and third direction.

Figure 5A:
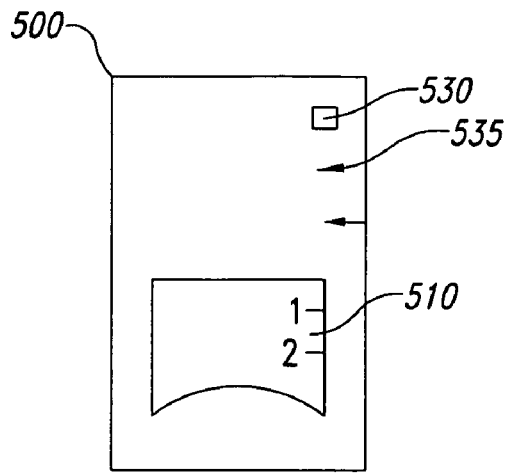
FIG. 5A–5D show a top view of another exemplary enclosures with an access piece positionable at a plurality of positions.

An enclosure is also provided with an access piece positionable at a plurality of positions. Referring to FIG. 5A, an enclosure 500 is shown with an access piece 510 in a closed position, completely covering the sensor (not shown). The enclosure also comprises a stopper 530 that operates to stop the access piece 510 at an open position. An arrow 535 marks a position on the enclosure 500, and a "1" and a "2," or other such alignment marks, mark two positions on the access piece 510. By aligning the access piece 510 markers "1" or "2" with the arrow 535, the access piece 510, in this case a sliding door, is positionable at multiple predetermined positions.

Figure 5B:
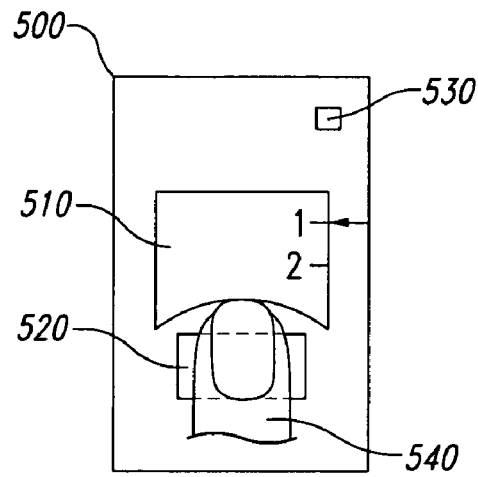
Figure 5C:
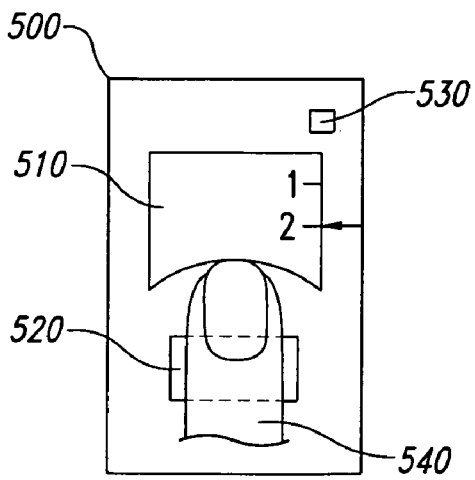
Figure 5D:
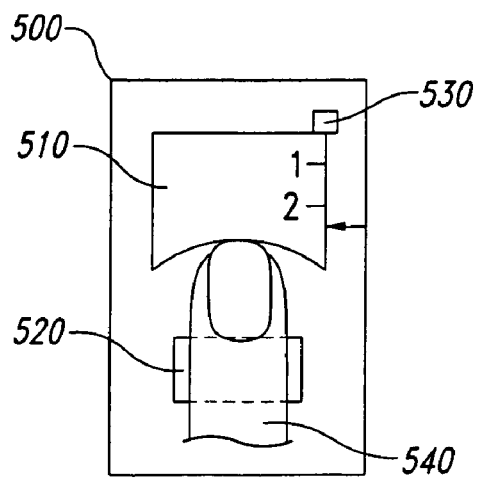

This multiple position capability enables capture of different portions of the fingerprint during enrollment. (Recall that enrollment is the procedure by which a fingerprint image is captured and stored as computer accessible data.) In FIG. 5B, the enclosure 500 is shown with the access piece 510 positioned at position "1." Only the tip of the finger 540 extends beyond the sensor 520, and the finger 540 and sensor 520, access piece 510 and finger 540 are positioned such that the top of the fingerprint image is captured. FIG. 5C shows the relative positions of the sensor 520, access piece 510 and finger 540 when the access piece 510 is at position "2." The finger 540 is positioned such that the fingerprint core is centered on the sensor 520, permitting capture of this portion of the fingerprint. In FIG. 5D, the access piece 510 is pushed to the stopper 530 and the finger 540 and sensor 520 are positioned such that an image of the bottom of the fingerprint is captured.

Figure 6:
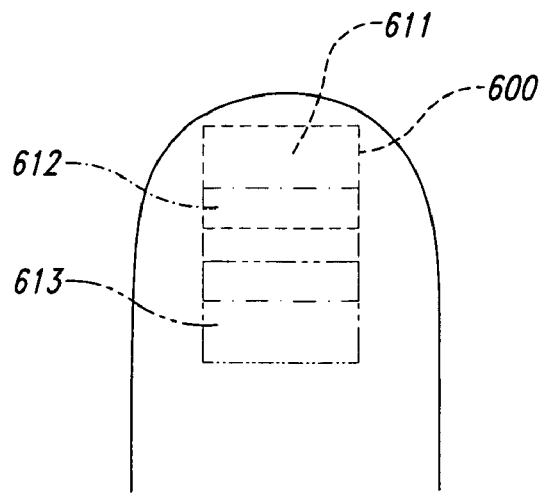
FIG. 6 shows a fingerprint image enrolled according to a method disclosed herein.

This procedure enables enrollment and reconstruction of a fingerprint image that comprises the combination of the images captured in position "1," position "2," and at the stop 530 position. This reconstructed image is called a virtual image. The virtual image is advantageously larger than the sensor area. For example, the virtual image 600 of FIG. 6 was captured and reconstructed according to the just-described procedure. As can be seen, the virtual image 600 is the combination of three overlapping images 611, 612 and 613, each of which is the size of the sensor.

Advantageously, the resulting image 600 has a larger area than the sensor. When a user places a finger on the sensor during an access procedure, alignment errors are overcome by the relatively larger area of the virtual image 600. In other words, the described apparatus and method increases the probability that the portion of the fingerprint placed on the sensor during an access procedure overlaps the enrolled image 600.

Figure 7:
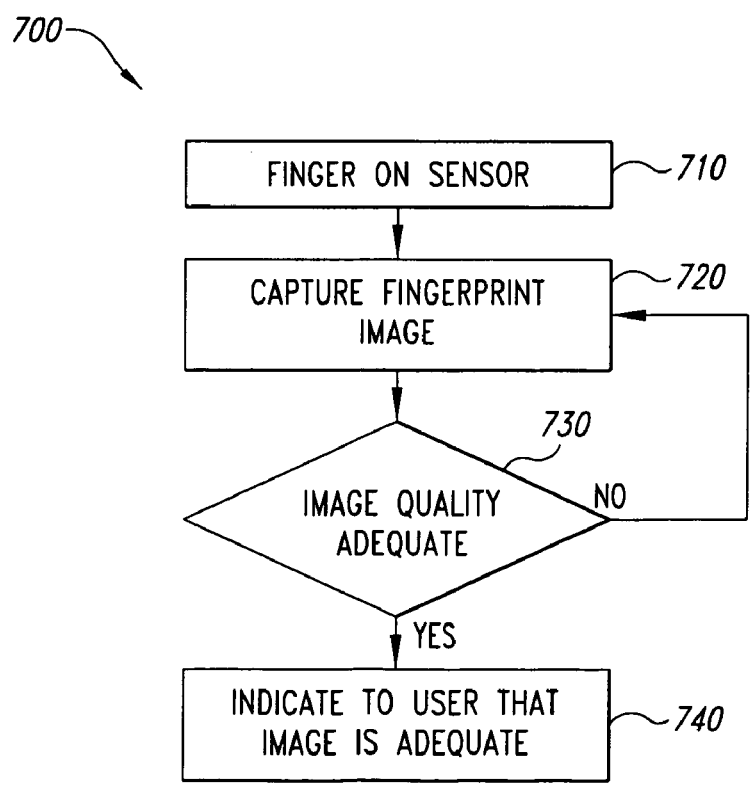
FIG. 7 is a flowchart illustrating one exemplary method of operating a sensor.

The advantages in overcoming finger placement error with the alignment features are further enhanced with an image quality indicator, which informs the user when an acceptable image has been captured. A method for providing an image quality indicator is described with reference to the flow chart 700 of FIG. 7. In a first step 710 of the procedure, the finger is placed on a sensor enclosed with the previously described apparatus. In step 720, the fingerprint image is captured. Then, the quality of the image is evaluated in step 730, where it is determined whether the image quality is adequate. If the image is adequate, then the user is advised in step 740 that the image has been captured. When the image is inadequate, control returns to the process step 720 and the procedure is repeated.

For purposes of this quality indicator feature, it is unimportant how an image is captured. For instance, contrast is one attribute commonly used for evaluating an image; the image is evaluated by how well the intensity range of the image stretches over the maximum intensity range available. Image evaluation is described in W. K. Pratt, "Digital Image Processing," Wiley Press, New York, N.Y., 1978, pp. 307–318. The process step 740, which informs the user whether the image quality is adequate, can also be implemented with various methods and apparatus. For instance, the indication may be audible, such as a beep emitted from a speaker, or visual, such as in lighting an LED.

Numerous modifications and alternative embodiments of the invention will be apparent to those skilled in the art in view of the foregoing description. For instance, an enclosure according to the invention is also operable to protect the sensor from dirt, dust or liquids. Similarly, the enclosure and access piece may also comprise a radio frequency shield to protect the sensor from electromagnetic energy.

What is claimed is:

1. An enclosure assembly for a fingerprint sensor, the enclosure assembly comprising:
    a stationary member including at least two substantially parallel sidewalls, the sidewalls partially defining a cavity in which the fingerprint sensor is disposed;
    a moveable access piece, which has a surface area larger than the surface area of the fingerprint sensor, the moveable access piece having a conductive portion electrically coupled to ground, wherein the moveable access piece is configured to move relative to the stationary member;
    a movement apparatus configured to maintain the moveable access piece in a position covering the fingerprint sensor and yet to allow motion of the moveable access piece relative to the stationary member so as to expose the fingerprint sensor; such that the moveable access piece is capable of defining at least two image alignment positions for the finger from which the fingerprint sensor can collect biometric information;

a switch configured to electrically couple a power supply to the fingerprint sensor after the moveable access piece exposes at least a portion of the cavity; and an image quality indictor communicatively coupled to the fingerprint sensor, the image quality indictor configured to obtain an image of a fingerprint, evaluate the image quality, and signal whether biometric information collected by the fingerprint sensor is acceptable.

2. The enclosure assembly of claim 1, wherein the movement apparatus comprises a spring to engage the moveable access piece and the stationary member, the spring configured to apply sufficient pressure to the moveable access piece so as to generally maintain the moveable access piece in the position covering the fingerprint sensor.

3. An enclosure assembly for a fingerprint sensor, the enclosure assembly comprising:

a stationary member including at least two substantially parallel sidewalls, the sidewalls partially defining a cavity in which the fingerprint sensor is disposed;

a moveable access piece, which has a surface area larger than the surface area of the fingerprint sensor, the moveable access piece having a conductive portion electrically coupled to ground, wherein the moveable access piece is configured to move relative to the stationary member;

a fingertip contour area located on a forward portion of the access piece, the finger contour area having a rounded, upper region configured to receive thereon a rounded tip portion of a fingertip; and a movement apparatus configured to maintain the moveable access piece in a position covering the fingerprint sensor and yet to allow motion of the moveable access piece relative to the stationary member so as to expose the fingerprint sensor such that the moveable access piece is capable of defining at least two image alignment positions for the finger from which the fingerprint sensor can collect biometric information.

4. The enclosure assembly of claim 3, wherein the movement apparatus comprises a spring to engage the moveable access piece and the stationary member, the spring configured to apply sufficient pressure to the moveable access piece so as to generally maintain the moveable access piece in the position covering the fingerprint sensor.

5. The enclosure assembly of claim 4, further comprising an image quality indictor means communicatively coupled to the fingerprint sensor, the image quality indictor configured to signal, whether biometric information collected by the fingerprint sensor is acceptable.

6. The enclosure assembly of claim 4, further including at least one image alignment guide configured to define a stop position for the moveable access piece.

7. The enclosure assembly of claim 3, further comprising a switch configured to electrically couple a power supply to the fingerprint sensor after the moveable access piece exposes at least a portion of the cavity.

8. The enclosure assembly of claim 3, wherein the moveable access piece has a first end and a second end, the first end having a concave surface portion configured to receive the fingertip.

9. The enclosure assembly of claim 3, wherein the movement apparatus comprises a motor that controls the motion of the moveable access piece relative to the fingerprint sensor.

10. The enclosure assembly of claim 1, wherein the movement apparatus comprises a motor that controls the motion of the moveable access piece relative to the fingerprint sensor.

11. The enclosure assembly of claim 1, further including at least one image alignment guide configured to define a stop position for the moveable access piece.

12. A method for enrolling a composite image of an object using a fingerprint sensor comprising the steps of:

receiving a finger disposed over a fingerprint sensor, the finger in a first stationary position;

capturing a first image of a first portion of the finger with the fingerprint sensor; causing the finger to be repositioned over the fingerprint sensor in a second stationary position;

capturing a second image of a second portion of the finger with the fingerprint sensor; and constructing a representative image of the finger from the first and second images, wherein prior to the step of receiving, the method comprises the step of discharging electrostatic energy from the finger through a moveable access piece disposed over the fingerprint sensor such that the moveable access piece is capable of defining at least two image alignment positions for the finger from which the fingerprint sensor can collect biometric information.

13. The method of claim 12, further comprising the step of engaging a power source with the fingerprint sensor after the moveable access piece is moved from a position protecting the fingerprint sensor.

14. The method of claim 12, further comprising the step of engaging a power source with the fingerprint sensor after the moveable access piece is moved from a position protecting the fingerprint sensor.

15. The method of claim 14, further comprising the step of disengaging the power source from the fingerprint sensor when the moveable access piece is returned to the position protecting the fingerprint sensor.

16. The method of claim 12, wherein the step of causing includes the steps of:

analyzing the first captured image for image quality; and providing a signal indicative of the image quality.

17. The method of claim 12, wherein the step of causing includes the step of repositioning a moveable access piece that slides relative to the fingerprint sensor.

18. The method of claim 12, wherein the step of causing includes the step of providing an alignment guide for aligning a moveable access piece with respect to the fingerprint sensor.

19. The enclosure assembly of claim 3 wherein the fingertip contour area is positioned in a location to align the core of the fingertip with the sensor when the access piece is moved to an open position.

20. An enclosure assembly for a fingerprint sensor, the enclosure assembly comprising:

a stationary member including at least two substantially parallel sidewalls, the sidewalls partially defining a cavity in which the fingerprint sensor is disposed;

a moveable access piece, which has a surface area larger than the surface area of the fingerprint sensor, the moveable access piece having a conductive portion electrically coupled to ground, wherein the moveable access piece is configured to move relative to the stationary member;

a fingertip contour area located on a forward portion of the access piece, the finger contour area having a rounded, upper region configured to receive thereon a rounded tip portion of a fingertip;

a movement apparatus configured to maintain the moveable access piece in a position covering the fingerprint sensor and yet to allow motion of the moveable access piece relative to the stationary member so as to expose the fingerprint sensor, such that the moveable access piece is capable of defining at least two image alignment positions for the finger from which the fingerprint sensor can collect biometric information; and an image quality indicator communicatively coupled to the fingerprint sensor, the image quality indictor configured to obtain an image of the fingerprint, evaluate the quality of the image and output a signal whether biometric image collected by the fingerprint sensor is acceptable.

* * * * *